United States Patent
Calvert

(10) Patent No.: US 6,820,671 B2
(45) Date of Patent: Nov. 23, 2004

(54) APPARATUS AND METHOD FOR ASSEMBLING ABSORBENT GARMENTS

(75) Inventor: Mickey W. Calvert, Norcross, GA (US)

(73) Assignee: Paragon Trade Brands, Inc., Norcross, GA (US)

( * ) Notice: Subject to any disclaimer, the term of this patent is extended or adjusted under 35 U.S.C. 154(b) by 0 days.

(21) Appl. No.: 09/970,704

(22) Filed: Oct. 5, 2001

(65) Prior Publication Data

US 2003/0066609 A1 Apr. 10, 2003

(51) Int. Cl.[7] .......... B32B 31/10; B32B 35/00; B65G 47/02; B65G 29/00; B65G 37/00
(52) U.S. Cl. .......... 156/543; 198/419.2; 198/471.1; 198/475.1; 198/478.1; 198/624
(58) Field of Search .......... 156/519, 538, 156/543, 515, 516, 379.6; 198/418.7, 419.2, 470.1, 471.1, 473.1, 474.1, 475.1, 478.1, 623, 624, 688.1, 689.1, 794, 792, 867.01, 867.02, 418.8, 479.1, 621.3, 631.1, 722, 723, 724, 793, 803.3, 803.4, 803.5; 29/16, 100

(56) References Cited

U.S. PATENT DOCUMENTS

| | | | |
|---|---|---|---|
| 3,960,646 A | | 6/1976 | Wiedamann |
| 3,960,647 A | | 6/1976 | Faure et al. |
| 4,578,133 A | * | 3/1986 | Oshefsky et al. ........... 156/164 |
| 4,726,874 A | | 2/1988 | VanVliet |
| 4,726,876 A | * | 2/1988 | Tomsovic, Jr. .............. 156/552 |
| 4,758,293 A | * | 7/1988 | Samida ...................... 156/73.1 |
| 4,925,520 A | * | 5/1990 | Beaudoin et al. ........... 156/494 |
| 4,973,326 A | | 11/1990 | Wood et al. |
| 5,177,841 A | * | 1/1993 | Hamuro et al. ............. 29/25.42 |
| 5,415,716 A | | 5/1995 | Kendall |
| 5,429,694 A | | 7/1995 | Herrmann |
| 5,492,591 A | | 2/1996 | Herrmann et al. |
| 5,531,850 A | | 7/1996 | Herrmann |
| 5,643,396 A | * | 7/1997 | Rajala et al. ................ 156/361 |
| 5,850,771 A | * | 12/1998 | Killian .......................... 83/23 |
| 6,149,755 A | | 11/2000 | McNichols et al. |
| 6,165,306 A | | 12/2000 | Rajala |
| 6,450,321 B1 | | 9/2002 | Blumenthal et al. |
| 6,520,236 B1 | | 2/2003 | Rajala |
| 6,524,423 B1 | | 2/2003 | Hilt et al. |
| 6,527,902 B1 | | 3/2003 | Rajala |

* cited by examiner

Primary Examiner—Sing P Chan
(74) Attorney, Agent, or Firm—Hunton & Williams

(57) ABSTRACT

An apparatus and method for assembling absorbent garments are disclosed. The invention uses an applicator having one or more heads that are adapted to hold parts. The applicator is rotated by a motor, which is controlled by a control device. The control device is operated such that the applicator heads pick up parts at one location at a first speed, and deposit the parts at a second location at a second speed.

28 Claims, 6 Drawing Sheets

APPARATUS AND METHOD FOR ASSEMBLING ABSORBENT GARMENTS

FIELD OF THE INVENTION

The present invention generally relates to absorbent garment and textile manufacturing. In particular, it relates to an apparatus and method for using a variable speed device to apply material to a moving web.

BACKGROUND OF THE INVENTION

Fabrics, such as textiles, woven materials and nonwoven materials constructed from natural or synthetic fibers, may be processed into garments or other assemblies by feeding them through processing lines. It is often desirable to operate these processing lines non-stop or with few interruptions. In many instances when a product being made in the processing line includes fabric or other sheet-like material, these materials are stored in roll form and fed into the line as a continuously moving web of material. When the roll runs out of fabric, a substitute roll may be spliced into the line with or without interrupting the activity of the line. The web may be processed in any number of ways, such as by folding, pinching, bonding, gluing, compressing, sewing, cutting, and the like. In many cases it is preferred that these operations be performed in the machine direction, that is, done in the direction that the material is moving without interrupting the constant flow of fabric along the line.

In many cases it may desirable to apply an intermittent supply of objects to a continuously moving web or to another intermittent supply of objects. For example, in the case of a diaper or other absorbent garment, it may be desirable to apply discrete units (i.e., objects that are not part of a continuous integral supply of material, or which have been severed from such a supply before being introduced to the continuously moving web) in particular locations on the moving web. In the field of absorbent garment manufacturing, typical discrete units include absorbent cores, transfer layers, adhesive tabs, and the like. In many cases, the units may themselves be formed as a continuous supply web that is severed into discrete units prior to being applied to the continuously moving web. The latter operation is sometimes referred to as a "cut and place" operation.

The supply of units may be provided at a greater or slower rate, as measured in terms of a linear feed rate, than the continuously moving web. For example, a moving web may have a linear speed of 100 feet per second (fps), and the supply of units may be provided at a rate of only 10 fps. In still other operations, the units may be stationary when they are supplied. In these operations, it may be desirable to accelerate or decelerate the units to the speed of the moving web prior to depositing them on the web.

Current placing devices are typically operated such that their surface velocity matches either the speed of the units as they are initially supplied, the speed of the moving web, or some intermediate speed. Such a device is disclosed, for example, in commonly assigned U.S. Pat. No. 5,415,716 issued to Kendall on May 16, 1995, which is hereby incorporated by reference in its entirety and in a manner consistent with the present invention. Such devices have certain drawbacks. For example, when the units or the web come into contact with a placing device having a different surface velocity they may be subjected to potentially harmful forces, such as impacts, friction, tension, compression, and the like. The units and the web may also damage one another when they contact each other at different speeds, and the differential speed may complicate the joining of the two.

Other currently available placing devices operate at a variable speed so that the units are picked up at one speed and deposited at another speed. For example, one available device, an eccentric path device, uses a number of arms extending from a central rotating hub. The arms are adapted to extend and contract radially while the hub maintains a constant angular velocity, thereby increasing and decreasing the linear velocity of the end of the arms. Units are picked up at one location, such as when the arms are extended, and deposited at the other location, thereby transferring the units between conveyors having a speed differential between them. Although such eccentric path devices may reduce the incidence of harmful forces on the units and the web, they have several disadvantages. For example eccentric path devices require relatively complex and heavy actuation devices that may be difficult or expensive to produce and maintain. Furthermore, eccentric path devices are typically limited by space constraints and mechanical limitations to operating across a relatively narrow speed differential. Even further, such devices can not be modified to operate with different products or at different speeds without making extensive modifications to the device and possibly to the rest of the manufacturing line, making even slight adjustments expensive and difficult.

These and other devices have been used in the particular context of the absorbent garment manufacturing industry. Absorbent garments, such as diapers, adult incontinence products, feminine care products, and the like, are often manufactured from continuous webs of nonwovens and film material. It is often desirable to produce these garments at as great a rate as possible, and so it is desirable to provide an applicator that can operate efficiently and at a high rate of speed.

It would be desirable to provide an improved method and system for cutting and placing material on a continuously moving web that does not subject the various parts of the assembly to harmful differential surface speeds. It would further be desirable for such a method and system to place units cut from a first web moving at a first speed onto a second web moving at a second speed that is greater or less than the speed of the first web. It would also be desirable for such a system to be easily adapted to operate in different manufacturing lines and to operate at different speeds. It would further be desirable to provide such a method and system at an economical cost. The present invention may be employed to provide these and other benefits.

SUMMARY OF THE INVENTION

The features of the invention generally may be achieved by an apparatus for assembling absorbent garments having an applicator that is rotated by a motor. The applicator has one or more heads, each of which is adapted to hold absorbent garment parts. A control device controls the rotation of the motor.

The control device rotates the motor, so that the one or more applicator heads travel at a first speed at a first location to pick up one or more parts moving at approximately the first speed, and travel at a second speed at a second location to deposit the one or more parts onto one or more targets moving at approximately the second speed.

In one embodiment, the applicator may have two heads.

In various embodiments, the heads may have gripping devices on them, such as vacuum grips or mechanical grips, or a combination of gripping devices.

In other embodiments, the motor may be an AC servo motor, and the control device may include an AC servo drive.

In various embodiments, the one or more parts may be grip tabs, absorbent core substrates or absorbent core assemblies, which may be deposited onto tissue layers, absorbent cores, and garment chassis layers. And in further embodiments, the one or more targets may be continuous webs of target material, or a series of discrete target objects.

In various embodiments, the first speed may be greater or less than the second speed. The first speed may be equal to about 3% to about 75% of the second speed, or may be equal to about 10% to about 50% of the second speed, and may be equal to about 20% of the second speed.

In various embodiments, the first speed may be about 20 feet per minute to about 1,000 feet per minute and the second speed may be about 50 feet per minute to about 3,000 feet per minute. In other embodiments, the first speed may about 40 feet per minute to about 650 feet per minute and the second speed may be about 1,000 feet per minute to about 2,000 feet per minute. In still other embodiments, the first speed may be about 65 feet per minute to about 328 feet per minute, and the second speed may be about 1,686 feet per minute.

In still other embodiments, the heads may be equipped with cutting devices to sever parts from a continuous supply web. The heads may also be equipped with bonding devices, such as portions of ultrasonic bonding devices.

BRIEF DESCRIPTION OF THE DRAWINGS

The features and advantages of the invention will become readily apparent when the detailed description is read in conjunction with the drawing figures, in which.

DETAILED DESCRIPTION OF THE PREFERRED EMBODIMENTS

Figure 1:
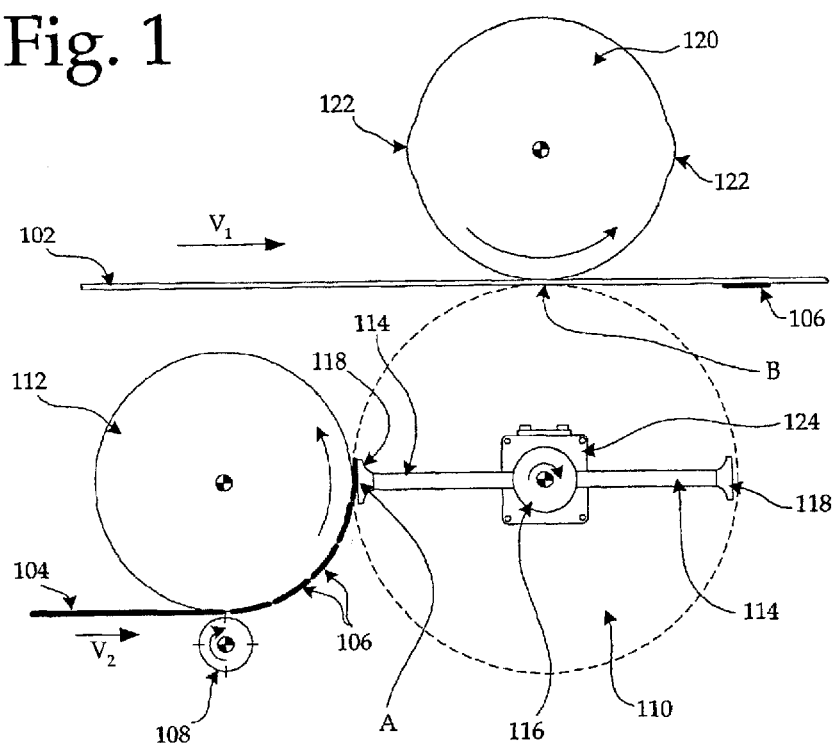
FIG. 1 is an embodiment of the present invention as viewed from the cross-machine direction with arrows denoting the movement of the various parts, showing the applicator picking up a unit.

As understood herein, "processing line" or "line" refers to any manufacturing or assembly line. Such a processing line may operate substantially non-stop, and may move in substantially one direction, or may operate in several directions. Such lines typically have one or more continuous webs of material, sometimes referred to as carrier webs, that carry other continuous or intermittent supplies of material along the line. For example, a main carrier web of material may serve as the foundation for constructing a series of garments, as the many parts of the garment are added to the main carrier web. Additional carrier webs may be used to create other units that are added to the main carrier web. Supplies of material may be fed into the line to join the one or more carrier webs, at any location and from any direction, and as a continuous supply or as an intermittent supply of units.

The material fed into the line is generally processed, such as by cutting, joining, folding or stacking the material at various processing stations. Each processing station may process the material in one or more ways. Waste material, such as fabric cutouts, may be removed from the line at any point. The present invention may be used with any processing line, and the following description is not intended to limit the scope of the application of the invention. The various processing stations may be operated substantially independently of one another, or they may be partially or entirely integrally controlled by a single driving system having a relatively small number of partially or wholly-independent controllers. Such a system may be based on a modular system such as those disclosed in commonly assigned U.S. Pat. Nos. 5,492,591 and 5,383,988, both issued to Hermann et al. on Feb. 26, 1996 and Jan. 24, 1995, respectively, and both of which are incorporated herein by reference in their entirety and in a manner consistent with the present invention.

The "machine direction," as used herein, is the primary direction in which material is traveling through the processing line at any given point. The material moving through the processing line generally originates from the upstream direction and moves in the downstream direction as it is processed. The "cross-machine direction" or "cross direction" is perpendicular to the machine direction.

As used herein, "web" refers to any substantially continuous supply of material that is fed through a processing line. A web may comprise, for example, woven cloth, nonwoven material, foam, mesh, film, paper, tissue, thin plastics and elastics, and the like. The web may be a single layer of material, supplies of material joined in series, or an aggregation or laminate of materials, in which case the supplies of materials constituting the web may themselves be continuous or non-continuous, and may include discrete (i.e., non-continuous) units distributed in a spaced-apart manner along the machine direction or cross-direction of the web. The web may be conveyed along the line by any means known in the art, such as by pinch rollers, vacuum drums, foraminous vacuum belts, and the like, or a combination of such devices. The conveyance means may be driven by interlinked or individual power transmission devices controlled independently or collectively by any type of drive control system.

As used herein, the term "unit" refers to any object that is picked up, conveyed, and deposited by an apparatus of the present invention. The term "target" refers to an object or object onto which an apparatus of the present invention applies units. A target may be, for example, a continuous or discontinuous supply of product assemblies onto which the units are affixed, or another conveying device.

As used herein, the terms "absorbent garment" and "absorbent article" refer to devices that absorb and contain body fluids and other body exudates. More specifically, these terms refer to garments that are placed against or in proximity to the body of a wearer to absorb and contain the various exudates discharged from the body. A non-exhaustive list of examples of absorbent garments includes diapers, diaper covers, disposable diapers, training pants, feminine hygiene products and adult incontinence products. Such garments may be intended to be discarded or partially discarded after a single use ("disposable" garments). Such garments may comprise essentially a single inseparable structure ("unitary" garments), or they may comprise replaceable inserts or other interchangeable parts. The present invention may be used with all of the foregoing and other classes of absorbent garments, without limitation, whether disposable or otherwise.

The embodiments of the invention described herein may be used in conjunction with a processing line that processes nonwoven materials and other materials into absorbent garments. The present invention may also be used with other types of processing line, as will be evident to those skilled in the art.

For clarity, features that appear in more than one Figure have the same reference number in each Figure.

The present invention deals particularly with the portion or portions of a processing line that places discrete units onto a moving target web or onto another supply of moving target objects. The present invention also may be used to decelerate units and place them onto a stationary target. The units may be supplied directly to an apparatus of the present invention, or may be fed through a portion of the processing line or through a separate processing line prior to being provided thereto. The units may enter the line as a continuous supply of material that is severed or otherwise processed into discrete units, or may be provided to the line as discrete units. The units may be supplied to an apparatus of the present invention in a substantially contiguous manner or spaced apart from one another. The units may comprise any portion of a product, or any other device or object, that is desired to be applied to the target or targets passing along the processing line.

In a preferred embodiment, the present invention comprises an apparatus that is configured to pick up units moving at one linear speed, and deposit them onto a target or targets moving at a different linear speed. A portion of the apparatus is preferably adapted to travel at approximately the same speed as the units as it picks them up, and then accelerates or decelerates to approximately the speed of the target in order to deposit the units onto the target. The speed of the apparatus may not be required to exactly match the speed of either the units or the target in order to still work properly. The degree to which the apparatus should match the unit and target speeds may vary between applications, and may depend on the physical properties of the unit and target and the features and functions of the processing line. Ideally, the speeds are matched such that the units and web are not damaged to a degree that will impact the performance of the product being manufactured by the processing line, and the units are properly placed on the web without misalignment, wrinkling, stretching, tearing, or other defects. By using the present invention, damaging forces and defective placement may be reduced, thereby allowing the transfer and application of lighter, more delicate units. A skilled artisan will be able to determine the proper degree to which the apparatus should match the speeds of the units and targets through routine experimentation in light of the teachings provided herein.

Figure 2:
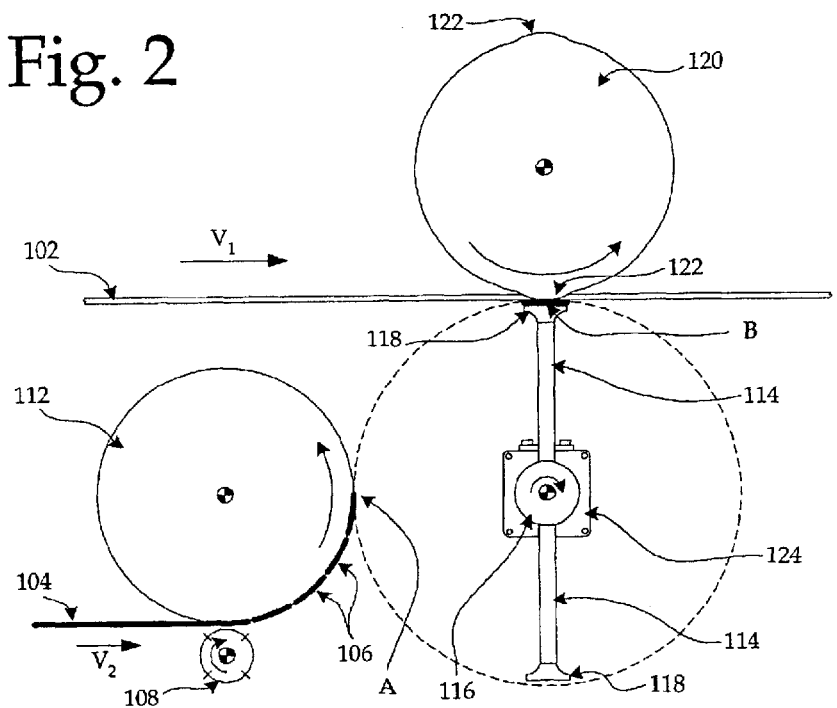
FIG. 2 depicts the embodiment of FIG. 1 showing the applicator depositing a unit onto a target web.

The general operation of the invention is described herein with reference to FIGS. 1 and 2, which are cross-direction views of a portion of an exemplary processing line that applies units 106 to a target web 102. In a preferred embodiment, the units 106 are placed on the target web 102 at periodic intervals so that the units 106 are located in a spaced-apart manner along the target web 102.

The target web 102 may comprise one or more layers of fabric or other material moving at a first linear speed $V_1$. For example, the processing line of FIG. 1 may be part of an absorbent garment processing line. In such a case, the target web 102 may comprise a single sheet of material, such as a tissue layer that forms the outer layer of the absorbent cores for absorbent garments, or a carrier web that forms the chassis of absorbent garments. The target web 102 may also comprise overlaid fabric webs, such as the overlaid topsheet, backsheet, elastic strands and absorbent core material of absorbent garments. In a preferred embodiment, the target web 102 is processed as a continuously moving web that travels in the machine direction; that is, the target web 102 essentially does not stop moving during processing. The target web 102 may also be processed, however, as an intermittently stopping web, in which case the web or a portion thereof may be stopped periodically to perform particular operations.

Figure 3:
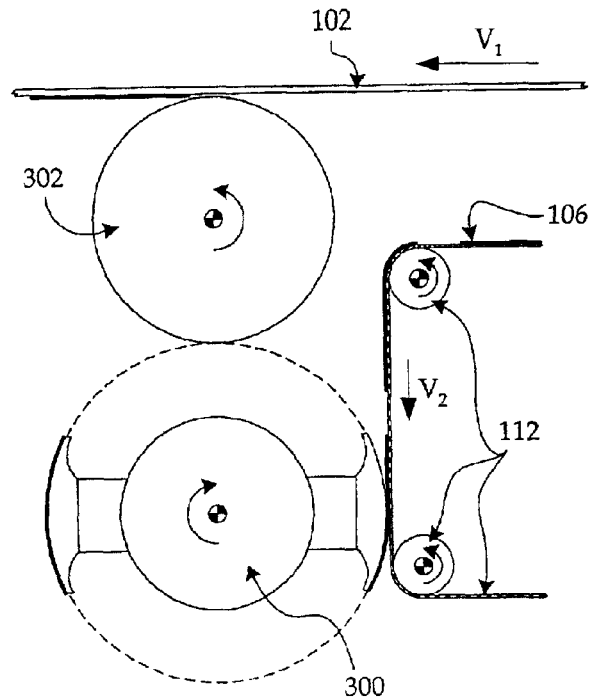
FIG. 3 is another embodiment of the present invention as viewed from the cross-machine direction.

In another embodiment, the target web 102 may be replaced by a successive supply of discrete target objects or another conveying or processing apparatus (item 302 in FIG. 3). In such a case, the target objects may be placed on a processing line in a spaced-apart relation to one another, for example, by providing a succession of target objects on a continuously moving foraminous conveyor belt. Such target objects may also be placed on a carrier web to facilitate conveyance through the processing line.

A supply of units 106 is provided to the apparatus of the present invention. The units 106 may be provided moving at a second linear speed $V_2$, or may be stationary. The units 106 may be provided to the apparatus of the present invention in any suitable manner, as will be apparent to those skilled in the art.

The units 106 may be provided in the form of a supply web 104, as shown in FIGS. 1 and 2. The supply web 104 is a continuous supply of material that may be severed by a cutter 108, such as a rotating knife or other device, to form separate units 106. For convenience and cost effectiveness, it has been found that providing the units 106 as a supply web 104 and severing them with a cutter 108 just prior to application to the target web 102 may provide economic and manufacturing benefits under certain circumstances. The decision of when to sever the supply web 104 into discrete units 106 may be driven by the particular details of the processing line, and are not critical to the functioning of the present invention, which may be adapted to operate with these or any other suitable supply method. For example, in an alternative embodiment, the units 106 may be entirely separate from one another (i.e., not parts severed from the same supply web 104), but assembled to be adjacent to or near one another before being provided to the present invention.

In an embodiment in which a supply web 104 is severed into discrete units 106, the cutter 108 may be any suitable cutting device that can sever discrete units 106 from the supply web 104 with a sufficient cut quality and at a sufficient rate to meet the requirements of the processing line. The cutter 108 may be a rotary cutting device having one or more blades that press against the supply web 104 to sever it, such as is shown in the embodiment of FIGS. 1 and 2. Other cutting devices, such as reciprocating cutting edges, laser cutters, hydraulic cutters, ultrasonic cutters and thermal cutters may also be employed to sever the supply web 104. The apparatus of the present invention may also be adapted to operate in conjunction with a cutting device to sever the supply web, as is described elsewhere herein. Such devices are known in the art, and a skilled artisan will be able to employ a suitable device without undue experimentation.

The units 106 may be carried into the proximity of an apparatus of the present invention by a supply feeder 112. The supply feeder 112 may be a vacuum drum, as shown in FIGS. 1 and 2, a foraminous vacuum belt, a conventional conveyor belt, or any other suitable conveying device that can hold the units 106 and transport them to the apparatus of the present invention. The selection of the supply feeder 112 may depend upon the nature of the units 106 to be conveyed. Units 106 having different physical properties, such as weight, thickness, flexibility, surface tactile properties, porosity and other features may require different types of supply conveyor 112. For example, a relatively rigid unit 106 may not adhere to a vacuum drum having a relatively small radius, necessitating a larger drum diameter, or a highly porous material may not be suitably held by a vacuum, necessitating a mechanical or other holding device.

The present invention may be used with any suitable processing line in which a supply of units 106 is to be applied to a target web 102 or other target. FIG. 3 depicts another manufacturing line layout in which an embodiment of an apparatus of the present invention may be employed. In the configuration of FIG. 3, the units 106 are provided to the apparatus in a spaced-apart manner by a supply feeder 112, which is depicted as a conveyor belt, such as a conventional conveyor, foraminous vacuum conveyor, or other type of belt, but may also be a vacuum drum as shown in FIGS. 1 and 2 or any other suitable type of device. An embodiment of the present invention 300, conveys the units 106 from the supply feeder 112 and deposits them onto a target other than the target web 102, such as an intermediate conveyor device 302. The intermediate conveyor device 302 may comprise any suitable type of conveyor, such as a vacuum drum or conveyor belt, which may travel at the speed of the target web 102 and may be adapted to use mechanical, vacuum, electrostatic, or other devices for holding the units 106 as they are conveyed to the target web 102.

Referring back to FIGS. 1 and 2, an apparatus of the present invention may comprise an applicator 110 that is driven by a variable speed motor 124. The applicator 110 generally comprises a rotating structure having one or more applicator heads 118 that are attached to rotate on a pivoting hub 116. In the embodiment depicted in FIGS. 1 and 2, the applicator 110 comprises a pair of rigid arms 114 that join the hub 116 to the applicator heads 118. The applicator heads 118 are adapted to pick up one or more units 106 from the supply feeder 112 at location A and deposit them on the target web 102 at location B. In other embodiments of the invention, the applicator may have a single applicator head 118 or more than two applicator heads. Balance weights and vibration dampers may also be attached to the applicator 110 to reduce vibration in the applicator 110 and provide other benefits.

The applicator heads 118 travel through a substantially circular path (shown as a broken line); picking up units 106 at location A, and depositing them on the target web 102 at location B. FIG. 1 shows the applicator head 118 picking up a unit 106, and FIG. 2 shows the applicator head 118 depositing a unit 106 at location B. A bump applicator 120 may be used in conjunction with the applicator 110 assist with applying the units 106 to the target web 102, as is shown in FIGS. 1 and 2. The bump applicator may comprise, for example, a drum-like structure having raised bumps 122 that act to bring the target web 102 closer to the applicator heads 118 as they pass by, or prevent the target web 102 from moving away from the applicator heads 118. The movement of the applicator 110 and the bump applicator 120 may be coordinated such that the bumps 122 and heads 118 pass the targets web 102 at the same time.

Although locations A and B are shown in FIGS. 1 and 2 as being approximately 90 degrees from one another, it will be appreciated that other configurations may be used, and may be necessary if more or less than two applicator heads are employed, as described elsewhere herein.

It would be desirable to pick up the units 106, which are traveling at a second velocity $V_2$, and deposit them on the target web 102, which is traveling at a first velocity $V_1$, without generating undesirable loadings on either the units 106 or the target web 102. To accomplish this goal, the angular velocity of the applicator 110 of the present invention may be varied so that the velocity of the applicator head 118 matches the unit velocity $V_2$ while picking up the units 106, and matches the target web velocity $V_1$ while depositing the units 106 on the target web 102.

In an embodiment in which the present invention is used in conjunction with an absorbent garment manufacturing line, one or more apparatuses of the present invention may be adapted to convey grip tabs (units 106), as described elsewhere herein, to an absorbent garment backsheet (target web 102). In one such embodiment, the grip tabs may have a length (in the machine direction) of about 20 to about 100 millimeters, and preferably about 25 millimeters to about 51 millimeters. The backsheet in such an embodiment may be supplied as a continuous web of material that is severed after the grip tabs are placed thereon. The tabs may be placed on the backsheet at an interval of between about 260 millimeters and about 514 millimeters to produce various sizes of absorbent garment. In such an embodiment, the garments may be manufactured at any rate up to about 1000 garments per minute, and preferably at a rate of about 750 garments per minute. At 1000 garments per minute, the backsheet may travel at velocities of up to about 1,686 feet per minute, and the grip tabs may be provided at velocities of about 65 feet per minute to about 328 feet per minute.

Those skilled in the art will appreciate that the $V_1$ and $V_2$ may vary for different materials, and these velocities may be dictated or constrained by other considerations, such as speed limitations imposed by other processes occurring along the processing line. For example, $V_2$ may be anywhere from about 20 feet per minute to about 1,000 feet per minute and $V_1$ may be about 50 feet per minute to about 3,000 feet per minute. In other embodiments, $V_2$ may be anywhere from about 40 feet per minute to about 650 feet per minute and $V_1$ may be about 1,000 feet per minute to about 2,000 feet per minute. The relative speeds of $V_2$ and $V_1$ may also vary. For example, $V_2$ may be equal to about 3% to about 75% of $V_1$; and may be equal to about 10% to about 50% of $V_1$. In a preferred embodiment, V2 may be equal to about 20% of $V_1$.

A single embodiment of the present invention may be used to apply the grip tabs to the backsheet for all of the above production rates and backsheet and grip tab velocities. Such an applicator may be used when to accelerate the grip tabs to up to about 33 times their initial velocity $V_2$, and preferably may be used to accelerate the grip tabs to 4 to 5 times their initial velocity $V_2$ to match the backsheet velocity. Furthermore, such an applicator may be used to apply grip tabs even at very slow speeds, such as those experienced at startup and shutdown, which may reduce the number of wasted garments made during startup and shutdown.

Naturally, other size and speed combinations may be used for various applications and to meet the needs or specifications for particular garments. Such variations are within the scope of the present invention, and will be obvious to one skilled in the art based on the teachings provided herein.

Figure 4:
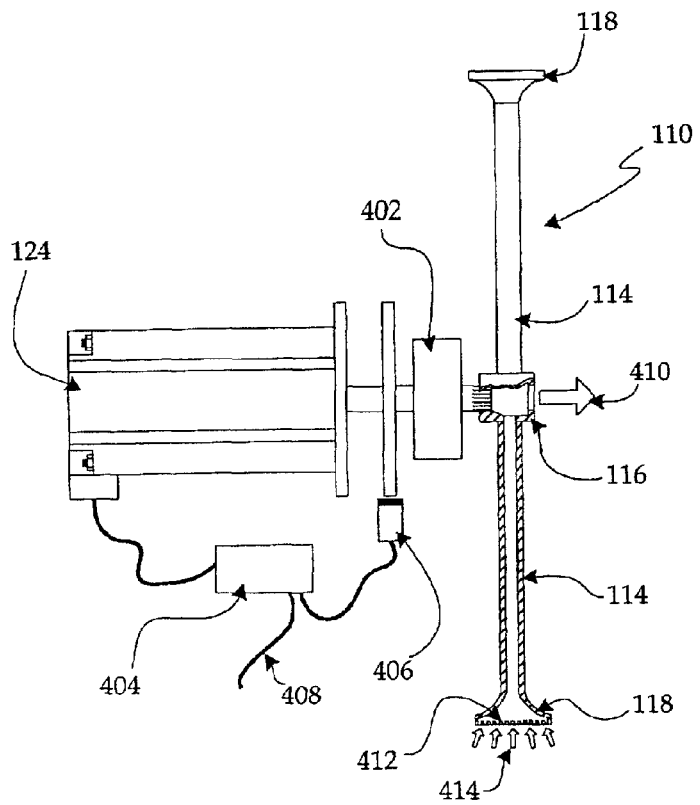
FIG. 4 is a partially cut-away view of an embodiment of the invention as viewed from the machine direction.

The applicator 110 and the motor 124 will now be discussed in more detail with reference to FIG. 4. In FIG. 4, there is shown a partially cut away depiction of an embodiment of the present invention as viewed from the machine direction. The applicator 110 is driven by a variable speed motor 124. The motor 124 may be coupled to the applicator 110 directly or through a power transmission device 402. The power transmission device may be used to change the gear ratio between the motor 124 and the applicator 110, and may include a decoupling device, such as a clutch. Although the embodiments herein depict the motor 124 being in proximity to the applicator 110, it will be understood that the motor 124 may be located remotely, and may operate the applicator 110 through devices such as shafts, belts, chains, and the like.

The motor 124 is preferably controlled so that the applicator 110 places each unit 106 at the desired location on the target web 102 or other target, requiring the movement of the applicator 110 to be coordinated with the movement of the target web 102. In a preferred embodiment, the motion of the motor 124 is controlled by a central processing unit (CPU) 404 that uses a feedback control algorithm to operate the applicator 110. The CPU detects and/or calculates the position and velocity of the motor 124, the applicator 110 and the applicator heads 118 and controls the operation of the motor 124 accordingly. One or more sensing devices 406 may be used to provide feedback information to the CPU 404. The sensing devices 406 may be integrated into the motor 124, may be separate devices, or may be otherwise disposed in the apparatus and processing line. Typical sensing devices 406 that may be used to provide position and velocity measurements are photoelectric eyes, electromagnetic sensors (e.g., Hall Effect sensors), and the like. Any other suitable sensing system may also be used. The CPU 404 may also be adapted to detect, calculate or receive information about the target web 102, the supply of units 106, or the operation of the remainder of the processing line from additional sensors or from an outside source 408. An outside source 408 may also provide operating instructions to the CPU 404. In one embodiment, an encoder on the main drive of a modular processing line provides input to the CPU 404 to inform the CPU 404 of the position and/or velocity of the main drive components. The CPU 404 may also be used to operate or control various other devices in the processing line.

In a preferred embodiment, the CPU 404 coordinates the movement of the applicator 110 and the target web 102 by using position feedback sensors (such as position resolvers) on each motor 124 to calculate and monitor the positions of the applicator heads 118 and receives information about the position of the target web 102 from another position resolver. The CPU 404 coordinates the locations of the applicator heads 118 with the target web 102 by employing a "unity" matching algorithm, in which the target web 102 and applicator heads 118 are controlled in terms of a per product basis, and not necessarily according to absolute linear velocities. Such control algorithms have been found to be useful in applications in which the processing line speed fluctuates or has local speed changes. For example, in an absorbent product processing line the carrier web may stretch during the manufacturing process, thereby requiring later parts of the line to operate at higher local linear velocities than earlier parts, while still operating at the same per product speed as earlier parts of the line.

The use of feedback control systems is known in the art, and a skilled artisan will be able to use such a system to control the speed of the motor 124 to obtain the benefits of the present invention.

In one embodiment of the invention, the motor 124 is an alternating current (AC) servo motor, and the CPU 404 comprises (at least in part) an AC servo drive. In such an embodiment, the sensors 406 may be internal parts of the AC servo motor. AC servo motors and drives are particularly useful in this application because they typically provide relatively accurate control over the position, velocity, and timing of the motor's movement, and thus may be used to accelerate and decelerate the applicator 110 with great accuracy. The position control feature of AC servo drives and motors may be particularly useful for obtaining the benefits of the present invention. An exemplary AC servo motor and drive system comprises an Allen-Bradley 1394 Turbo AC drive coupled with an Allen-Bradley 1326 AB 460V Torque Plus AC servo motor, both of which are available from Rockwell Automation, a company headquartered in Milwaukee, Wis. Other devices may be used to accelerate the applicator 110, such as a conventional AC or DC motor. Other devices may also be employed with the present invention to decelerate the applicator 110, such as electric, hydraulic, and friction brakes (not shown).

It may be desirable to minimize the amount of inertia that must be overcome by the motor 124 as it accelerates and decelerates the applicator. By doing so, less power may be consumed when accelerating and decelerating the motor 124 and applicator 110, and a cost savings may be realized. In addition, reducing the overall inertia may allow lower-powered AC drives and motors to be used, and may provide the apparatus with greater overall accuracy. The inertia of the present invention may be reduced, for example, by reducing the weight of the rotating components (such as by using arms 114 to hold the applicator heads 118 instead of a drum-like structure and using a low-inertia AC servo motor as the motor 124), locating the weight closer to the axis of rotation, employing lighter materials, and, in higher speed applications, by reducing the aerodynamic drag of the moving parts. The principles employed to design a low inertia system and reduce the inertia of existing systems are known in the art, and skilled artisans will be able to do so without undue experimentation.

Still referring to FIG. 4, the applicator 110 generally comprises one or more applicator heads 118 that are each attached to a rotating arm 114. The arms 114 may also be replaced with any suitably shaped structure, such as a drum having applicator heads attached to the outer face and the like. The heads 118 are preferably adapted to pick up the units 106, hold them as the applicator 110 accelerates or decelerates, and deposit them onto the target web 102 or other target surface. The heads 118 may also be adapted to pivot or rotate about one or more axes as they convey the units 106 to the target. The heads 118 may be flat, concave or convex, and may be contoured to match the shape of the units 106.

The heads 118 may use any suitable device or method to acquire, hold and deposit the units 106. For example, the heads 118 may have a perforated surface which may be used in conjunction with a vacuum source to hold the units 106 in place by suction. For example, as shown in the embodiment of FIG. 4, a vacuum source 410 may be connected to a perforated face 412 of the applicator head 118 through a passage in the arm 114, thereby creating an airflow 414 into the head 118 that holds the units 106 in place. When it is desired to release the unit 106, the vacuum source 410 may be intermittently disabled, such as by blocking off any of the vacuum passages. Other devices for holding the units 106 to the applicator head include hooks, pins, clamps, magnets, electromagnets and so on. A movable holding device may be operated by pneumatic, hydraulic, electrical, mechanical, or any other type of selectively controllable actuating device. Such holding devices are known in the art, and a skilled artisan will be able to provide applicator heads 118 having a suitable holding device without undue experimentation.

The particular details of the applicator head 118 design may vary depending on the physical properties of the units to be conveyed, and the present invention is not limited to the use of any particular applicator head 118 type or design. For example, in an embodiment in which an apparatus of the present invention is used to apply adhesively coated grip tabs to a diaper backsheet, a combination of a vacuum and pins may be used to hold the grip tabs as the applicator 110 conveys them. Other designs and uses for the applicator heads 118 will be apparent to those skilled in the art after reading the teachings herein.

The applicator 110 rotates such that the applicator heads 118 travel in a circular path, which is shown in the Figures as a broken line. The units 106 are supplied at a first location along the circular path (point A), and deposited on the target web 102 or other target at a second location along the circular path (point B). The relative locations of points A and B may be dictated by the number of applicator heads 118 and the particular acceleration and deceleration capacities of the applicator, as is described with reference to FIGS. 5, 6a, 6b, and 7.

Figure 5:
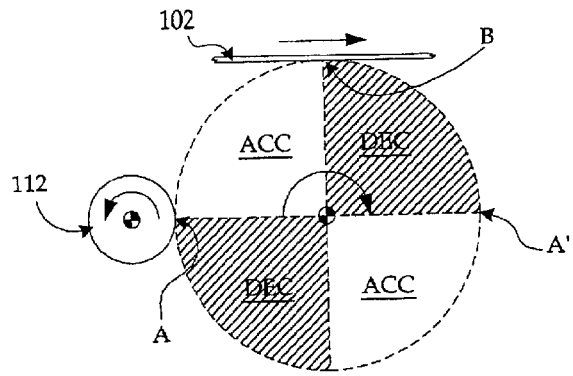
FIG. 5 is a schematic drawing showing the acceleration and deceleration zones of an embodiment of the present invention.
Figure 6A:
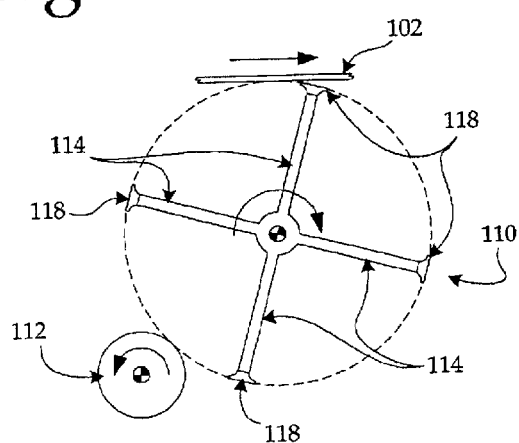
FIG. 6a is a four-head embodiment of the present invention as viewed from the cross-machine direction.
Figure 6B:
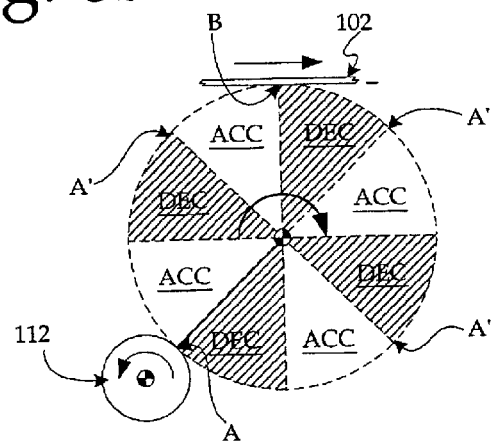
FIG. 6b is a schematic drawing showing the acceleration and deceleration zones of another embodiment of the present invention.

Referring now to FIGS. 5, 6a and 6b, the relationship between the number of applicator heads 118 and the locations of points A and B is demonstrated. FIG. 5 depicts the locations of the supply feeder 112 and the target web 102 in an embodiment in which the applicator 110 has two applicator heads 118 rigidly located on opposite ends of the applicator 110, such as is depicted in FIGS. 1, 2 and 3. (For clarity, the applicator is not shown in FIGS. 5 and 6b). Each head 118 of the applicator 110 picks up a unit 106 at point A, and is accelerated through an acceleration zone (marked as "ACC") to the speed of the web 102. After depositing the unit 106 at point B, the applicator 110 is decelerated in a deceleration zone (marked as "DEC") so that the speed of the second head 118 matches the speed of the supply feeder 112 as it passes point A.

As will be apparent from FIG. 5, in a two-head embodiment of the invention, the applicator must be accelerated and decelerated twice during each 360 degree revolution because each of the applicator heads must be slowed to the speed of the supply feeder 112 as it passes thereby. Furthermore, whenever one head 118 is slowed down, the other is slowed as well because they are rigidly connected to one another. For this reason there are two locations, points A and A', at which both heads are simultaneously traveling at their slowest speed, and the supply feeder (and thus the pickup point, point A) may be located at either one of these two locations. In FIG. 5 the acceleration and deceleration zones are the same size, and so point A is located 90 degrees prior to point B and point A' is located 90 degrees after point B. Those skilled in the art will appreciate that more or less applicator heads 118 may be used in the invention. For example, in the embodiment shown in FIG. 5, only on head 118 may be used, and the other side of applicator 110 may be designed to avoid contact with the units 106 or the web 102. In this case, only one acceleration zone and one deceleration zone would be necessary.

A four-head embodiment of the invention is shown in FIG. 6a. In this embodiment, the applicator 110 comprises four applicator heads 118 that are rigidly joined to one another by arms 114. As with other embodiments, the applicator 110 must be decelerated to the speed of the incoming units 106 each time an applicator head 118 passes the supply feeder 112, and accelerated to the speed of the web 102 each time an applicator head 118 passes thereby. Therefore, the four-head applicator should be accelerated and decelerated four times during each 360 degree rotation. As such, the heads 118 will be simultaneously slowed at four different points along their circumferential path. The embodiment of FIGS. 6a and 6b has equal sized acceleration and deceleration zones, and so the points at which the four heads 118 are traveling at their minimum speed are located at 135 degrees before point B, 45 degrees before point B, 45 degrees after point B, and 135 degrees after point B. In the embodiment of FIGS. 6a and 6b the supply feeder 112 is located at point A, but may alternatively be located at any of the points designated as point A'.

In the foregoing analyses, the supply feeder 112 and the target web 102 have been located at the points where the applicator hear 118 is at its minimum and maximum velocity, respectively. In other embodiments it may be desirable to locate the target web 102 at a point of minimum velocity, and the supply feeder at a point of maximum velocity. It will also be understood that the target web 102 and/or supply feeder 112 may be located at a location that is offset from the points of maximum and minimum velocity.

The proper relative locations for the web 102 (point B) and the supply feeder 112 (point A) for other embodiments of the invention having one arm, three arms, or more than four arms may be determined using an analysis similar to the foregoing analysis. It will be apparent to those skilled in the art, based on the present teaching, how to properly locate the components of a manufacturing line relative to one another for any particular embodiment of the present invention.

Figure 7:
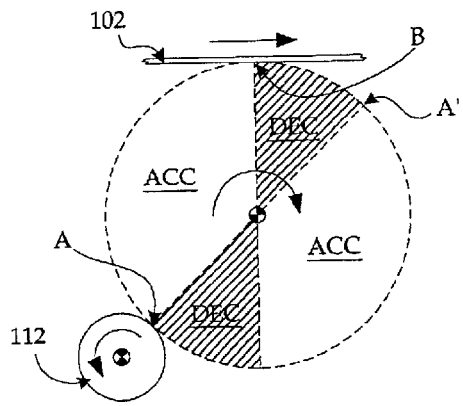
FIG. 7 is a schematic drawing showing the acceleration and deceleration zones of yet another embodiment of the present invention.

Referring now to FIG. 7, The relative locations of points A and B may also be influenced by the ability of the motor 124 to accelerate and decelerate the applicator 110. This relationship may be readily explained using the two-head applicator of FIGS. 1, 2, 3 and 5 as an example. In FIG. 5, the acceleration and deceleration zones are shown as being approximately the same size as one another. In the embodiment of FIG. 5, the motor 124 has the capability to accelerate the applicator from the discrete unit speed at point A to the web speed at point B in about 90 degrees of rotation. Similarly, the motor can decelerate the applicator 110 back to the discrete unit speed within another 90 degrees of rotation. If, however, the motor 124 is incapable of accelerating the applicator 110 within the 90 degrees of rotation provided, then point A may be advanced so that the motor 124 has more space in which to accelerate the applicator 110, as is shown in FIG. 7. In such an embodiment, a supplemental deceleration device may be employed, if necessary, to assist with decelerating the applicator in the reduced size deceleration zone.

Figure 8:
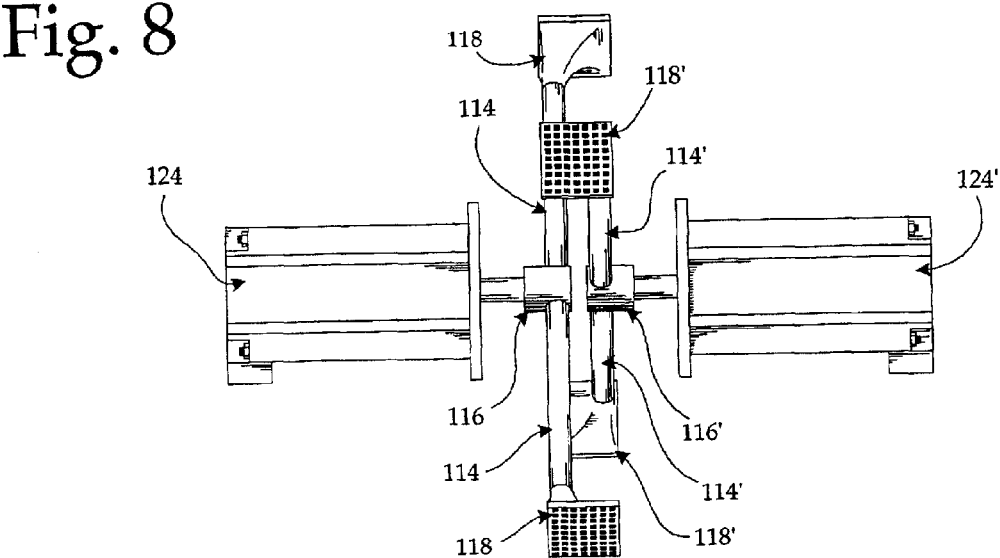
FIG. 8 is a dual-applicator embodiment of the present invention as viewed from the machine direction.

Referring now to FIG. 8, in another embodiment of the invention, a pair of applicators 110 may be operated face-to-face to increase the rate at which units 106 may be deposited on a target web 102 or other target. In such an embodiment, the two applicators 110 may be equipped with their own hubs 116, 116' to which arms 114, 114' and applicator heads 118, 118' are attached. Each applicator 110, 110' may be operated by a separate motor 124, 124' such that they rotate independently. An advantage of having independently operating applicators 110 is that the number of heads 118 may be increased without having to increase the number of accelerations and decelerations that each applicator 110 must undergo during each revolution.

In embodiments employing larger numbers of applicator heads 118 that are rigidly connected to one another, the motor 124 typically must be able to overcome a greater amount of inertial resistance to acceleration and deceleration. There are a number of reasons for this increased inertia. First, the greater number of heads 118 will likely increase the rotating mass of the applicator, thereby increasing inertial loads. Second, increasing the required number of accelerations and decelerations that must be made during each revolution necessarily reduces the room in which those accelerations and decelerations may be made, requiring greater force to provide a given amount of acceleration or deceleration. The inertial capacity of the motor 124 may thus be overloaded. By decoupling the applicator heads 118 from one another and providing a second motor, the embodiment of FIG. 8 may provide the additional capacity of an applicator 110 having additional heads 118, but without increasing the inertial loads on he motors 124, 124'.

Figure 9A:
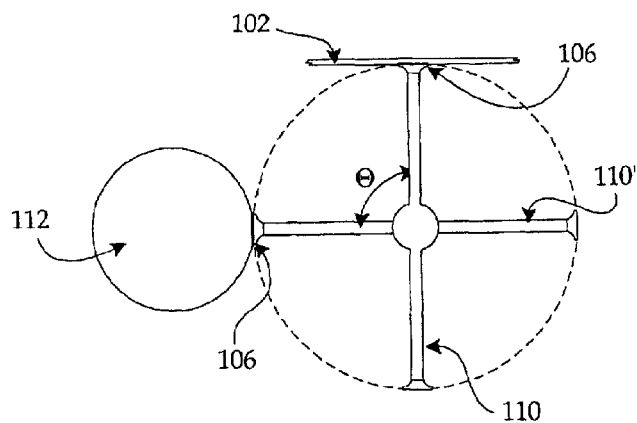
FIG. 9a is a dual-applicator embodiment of the present invention as viewed from the cross-machine direction shown in a first operating position.
Figure 9B:
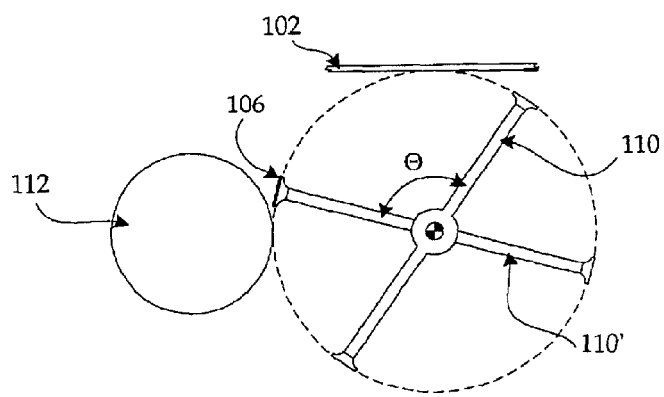
FIG. 9b is the embodiment of FIG. 9a shown in a second operating position.
Figure 9C:
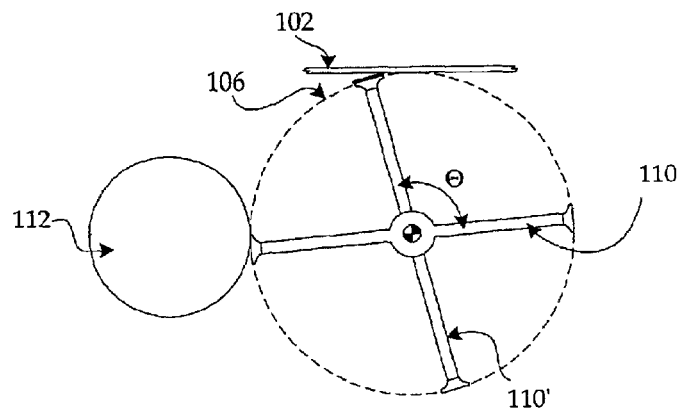
FIG. 9c is the embodiment of FIG. 9a shown in a third operating position.

The operation of the embodiment of FIG. 8 may be better understood with reference to FIGS. 9*a*, 9*b* and 9*c*, which show the applicator arms 110, 110' in various rotational positions. In FIG. 9*a* the first applicator 110 is depositing a unit 106 on a target web 102 at the same time that the second applicator 110' is picking up a unit 106 from a supply feeder 112. In FIG. 9*a*, the two applicators 110, 110' are oriented at right angles with one another, as indicated by angle Θ, however, the first applicator 110 is traveling at a greater angular velocity than the second applicator 110' so that its head speed matches the speed of the web 102. The second applicator 110' is rotating at a slower angular velocity so that its head matches the speed of the supply feeder 112. In FIG. 9*b*, the first applicator 110 is decelerating as it travels away from the web 102, and the second applicator 110' is accelerating as it traveling towards the web 102 (both applicators are moving clockwise in all circumstances). It can be seen that the angle Θ between the applicators 110, 110' increases for the first part of this travel because the first applicator 110 is still rotating faster than the second applicator 110'. In FIG. 9*c*, it can be seen that as the first applicator approaches 110 the supply feeder 112 and the second applicator 110' approaches the web 102 their relative speeds have reversed, and the second applicator 110' is now rotating faster than the first applicator 110, thereby decreasing the angle between them Θ. The change in the angle Θ between the two applicators 110, 110' may be described as a "scissoring" motion.

Although the two applicators 110, 110' of this embodiment have been described as being operated by two different motors 124, 124', they may also be operated by a single motor. If a single motor is used, the two applicators 110, 110' must be mounted such that they can be actuated independently of one another to obtain the desired scissoring motion. For example, the motor 124 may be rigidly attached to the first applicator 110, and the second applicator 110' may be pivotally mounted to the first applicator 110, but with a mechanically- or hydraulically-operated linkage that is actuated to provide the desired scissoring motion. Those skilled in the art will be able employ a multiple applicator embodiment of the invention without undue experimentation based on the teachings herein.

Embodiments of the apparatus and method of the present invention may be particularly useful in the absorbent garment producing industry. Absorbent garments typically contain a number of units that are attached to a continuously moving web of material.

Absorbent garments generally comprise a liquid pervious topsheet layer, a liquid impervious backsheet layer, and an absorbent core disposed between the topsheet and the backsheet. In order to fit the garment on a wearer, portions of the topsheet and/or backsheet may be adapted to provide the garment with a garment-like structure, or a topsheet/backsheet/core assembly may be applied to a chassis layer that forms a garment-like structure. The garment may be held to the wearer by providing a continuous waist belt, or by using an openable waist having a closure system to hold the waist together. A number of other absorbent garment configurations may also be used successfully, and the present invention may be used with any such configuration.

In order to manufacture absorbent garments, one or more layers of material may be provided into the manufacturing line as a carrier web to which the other layers and parts are attached, thereby forming a continuous supply of connected garments that are connected by the carrier web. Later in the assembly, the carrier web and any layers or units attached thereto may be severed from the continuous supply of garment bodies to form individual garments, and further processing may be done to the individual garments.

Embodiments of the present invention may be adapted to operate in absorbent garment manufacturing lines. In one embodiment, the present invention may be used to apply a supply of substrate layers to an absorbent core assembly. Substrate layers are often relatively expensive. Substrates also may be easily damaged by conventional placement devices, and so they may be designed to be more robust than necessary to survive manufacturing processes employing conventional placement devices. By using the present invention, the substrate layers may be made from less robust material, and may be made at less of a cost, because the substrates may be subjected to a reduced amount of damaging forces caused by contact with other objects at a differential speed.

Figure 10:
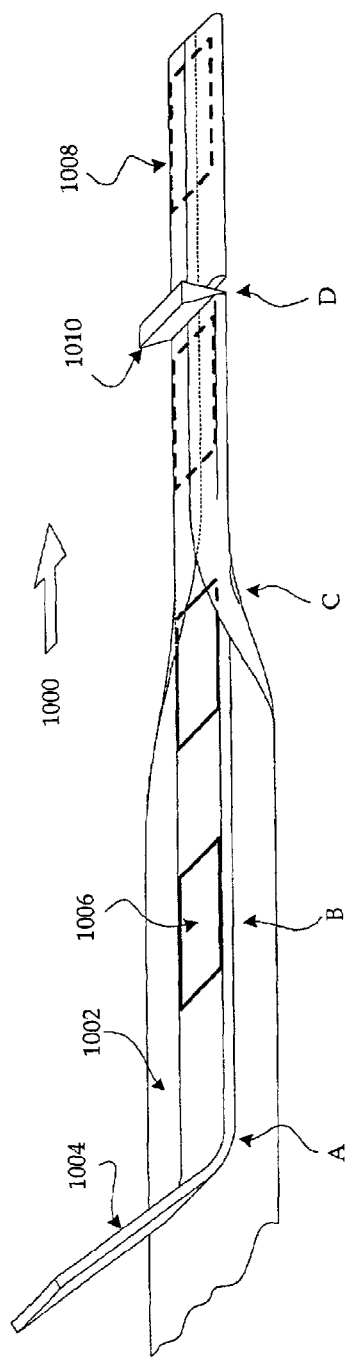
FIG. 10 is a drawing of an assembly process using an apparatus of the present invention.

FIG. 10 depicts a process for applying substrates to an absorbent core subassembly using an embodiment of the present invention. A continuous supply of tissue 1002 is provided along the machine direction 1000. At point A, a continuous supply of core material 1004 is laid on the tissue layer 1002. At point B, an embodiment of the present invention deposits discrete substrate layers 1006 on the core material 1004 in a spaced-apart manner. The substrate layers 1006 may be fluid transfer layers, barrier layers, porous films, or any other performance enhancing devices that are desired to be located on the surface of the core 1004. It will be apparent to those skilled in the art that the substrate layer 1006 may alternatively be applied to the supply of core material 1004 before the core material 1004 is placed on the tissue supply 1002, or the substrates 1006 may be placed on the tissue layer 1002 prior to the placement of the core material 1004 thereon. At point C, the supply of tissue 1002 is folded over the core material 1004 and substrates 1006. The tissue supply 1002 may be glued or otherwise treated to ensure that the folds stay closed. At point D, individual absorbent core subassemblies 1008 are severed from the supply by a cutting device 1010.

The flexibility of the present invention also allows it to be quickly and easily adapted to operate in different positions on the manufacturing line, and allows it to be adjusted to produce garments having different features and dimensions. For example, a single apparatus of the present invention may be able to convey different shape or size units 106, and may be modified to convey other shape and size units 106 simply by replacing or adjusting the applicator heads 118. Different target speeds $V_1$ and unit speeds $V_2$ may be accounted for by reprogramming the CPU 404. Different width products may be assembled using the same device by moving the device in the cross-machine direction to relocate the point at which the applicator heads 118 apply the units 106 to the target. Such modifications are typically less expensive than similar modifications that may be made to conventional application devices. For example, in order to change the speed differential across which a conventional application device operates, it is often necessary to completely rebuild the application device with different dimensions, and relocate other parts of the assembly line. The flexibility of the present invention is demonstrated herein with reference to FIG. 11, in which some of the many additional uses of the present invention are illustrated.

Figure 11:
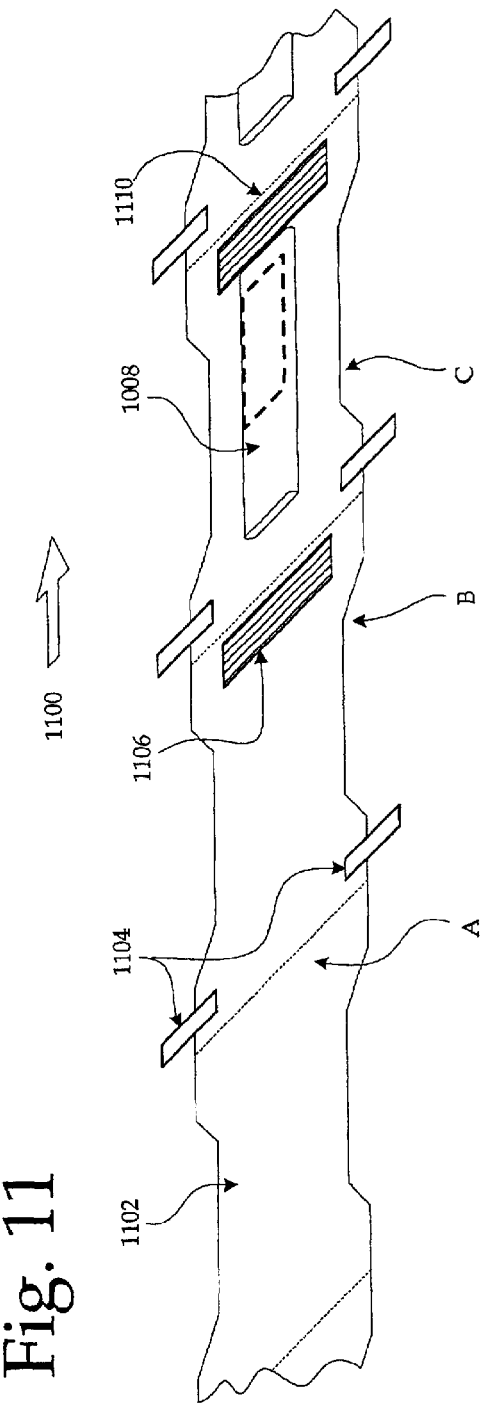
FIG. 11 is a drawing of a second assembly process using apparatuses of the present invention.

FIG. 11 depicts a process for assembling various absorbent garment components onto a continuous chassis layer supply 1102 that is moving in the machine direction 1100. The chassis layer supply 1102 is eventually severed along cut lines 1110, along with any overlying material, to create individual garments. The chassis layer supply 1102 may comprise any material suitable for use as an absorbent garment chassis layer, and that has sufficient strength in the machine direction to withstand forces generated during production. Nonwoven polymers are exemplary for this application, but other materials may be used.

At location A, one or more embodiments of the invention (not shown) may attach grip tabs 1104 to each side of the chassis layer supply 1102. In such an embodiment, The grip tabs 1104 may comprise any type of diaper fastening device, such as hook and loop fastener components, adhesive tapes, and the like. A separate apparatus of the present invention may be used to attach each grip tab 1104 or a single apparatus may be adapted to attach the tabs 1104. Such devices are known in the art.

At location B, another embodiment of the invention (not shown) may attach grip tab mating surfaces 1106 to the chassis layer supply 1102. The mating surfaces 1106 may be adapted to engage with grip tabs 1104 to fit the garment on an intended wearer. At location C, yet another embodiment of the present invention (not shown) may be adapted to place absorbent core assemblies 1008, such as those disclosed in FIG. 10 and the discussion relating thereto, onto the chassis layer supply 1102.

Embodiments of the present invention may also be used to attach other units or devices to the chassis layer supply 1102, as will be evident to those skilled in the art in light of the present teaching, and it will be understood that the invention is not limited to the applications disclosed herein.

The apparatus of the present invention may be adapted to provide various additional functions, in addition to those of conveying and placing the units 106. For example, embodiments of the invention may be adapted to assist with bonding, stretching, and cutting the units 106. Other functions may also be provided, and the invention is not intended to be limited to the following exemplary features.

It may be desirable to attach the units 106 to the target web 102, and the present invention may be adapted to assist with the attachment process. Many techniques and devices are available for attaching the various parts of absorbent products to one another. For example, the use of adhesives, ultrasonics, heat and combinations thereof to bond parts to one another are known in the art. In various embodiments, the present invention may be used to accommodate or facilitate these attachment operations. The method by which the units 106 may be joined to the target web 102 or other targets may vary between different applications and materials.

In an embodiment in which ultrasonic bonding is used, for example, an ultrasonic horn may be located opposite the applicator heads 118 as they deposit the units 106 onto the target web 102 to bond the units 106 in place, or the ultrasonic horn may be located in the applicator head 118 itself and an anvil may be placed opposite the head 118. The horn or anvil may also be integrated into the bumps 122 of a bump applicator 120. The applicator heads 118 may be patterned to provide a specific bond pattern. Similarly, in an embodiment using thermal bonding, the applicator heads 118 and the bump applicator 122 may comprise patterned heating elements to melt the units together.

Figure 12:
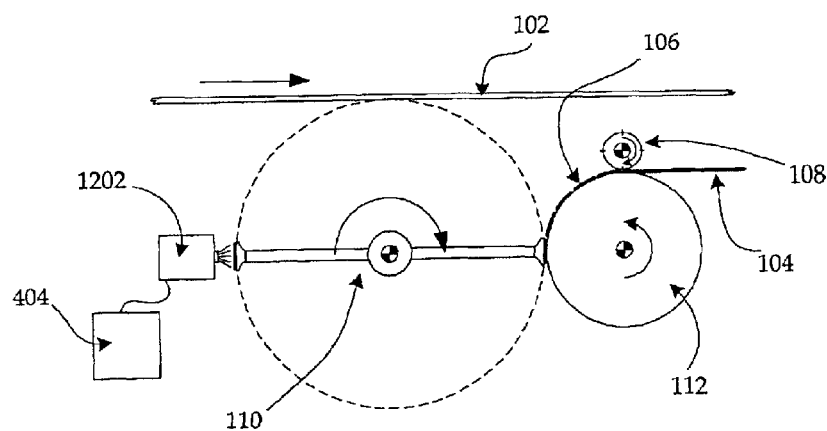
FIG. 12 is an embodiment of the present invention being used in conjunction with an adhesive spray applicator as viewed from the cross-machine direction; and, FIG. 13 is an embodiment of the present invention being used in conjunction with an adhesive activator as viewed from the cross-machine direction.

In an embodiment in which adhesive bonding is used, a spray of adhesive (which may be a hot-melt adhesive, a room-temperature tacky adhesive, or other type of adhesive) may be applied to the units 106 or the target web. For example, in the embodiment depicted in FIG. 12, a spray nozzle 1202 may apply a spray of adhesive to the units 106 as they are conveyed to the target web 102. The spray nozzle 1202 may be operated by, for example, an CPU 404 (which may be the same CPU 404 that controls the operation of the motor 124, or may be connected to that CPU or to a common control system), mechanical switches, or other control devices. A bump applicator (120 in FIG. 1) may be used to press the target web 102 against the units 106 and the applicator heads 118 to strengthen the bond between the web 102 and the units 106.

Figure 13:
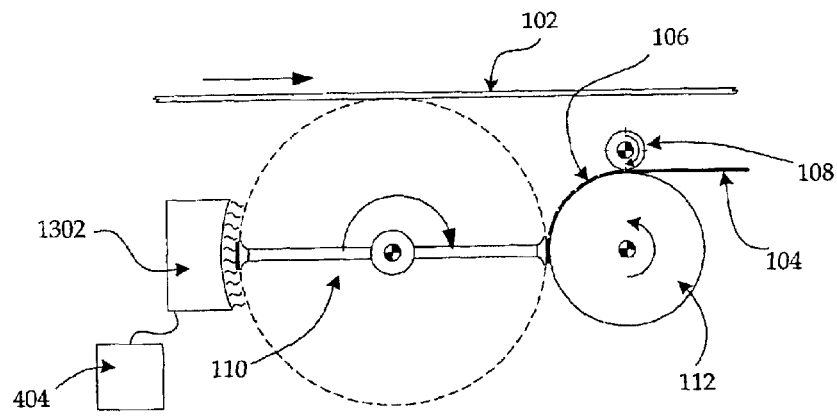

It may be desirable to pre-coat the units 106 with an adhesive that is non-tacky at room temperature, and that may be adhesively activated just prior to application to the target web 102. Such an embodiment may be useful to allow the units 106 to be stored and conveyed without adhering to each other or to parts of the processing line before being applied to the target web 102. Such adhesives are disclosed, for example, in U.S. Pat. No. 4,973,326 issued to Wood et al. on Nov. 27, 1990, which is herein incorporated by reference in its entirety and in a manner consistent with the present invention. For example, in the embodiment depicted in FIG. 13, the units 106 may be made having an integral layer of hot-melt adhesive of thermoplastic or other resin that is adhesively activated by an activation source 1302 as the units 106 are being conveyed to the target web 102. The type of activation source will depend on the type of non-tacky adhesive that is applied to the units 106, and may use heat, light, radiation, or other means to activate the adhesive.

The activation source 1302 may be located to provide efficient heating to the adhesive, such as by locating it at a point where the angular velocity of the applicator head is at a minimum. The activation source 1302 may be operated continuously or may be selectively controlled by an CPU 404 such as the CPU controlling the motor 124, mechanical switches, or other control devices.

In one embodiment of the invention, the applicator 110 may be adapted to hold the units 106 in a stretched, folded, or otherwise mechanically altered position at it conveys them to the target. For example, in some cases the supply feeder 112 may be used to stretch the unit 106 in one or more directions prior to being fed into the apparatus of the present invention. Such a stretching function may be useful, for example, when it is desired to apply an elastic member to the target web 102 in a stretched condition to thereby elasticize the target web 102. Examples of such a device are provided in commonly assigned U.S. Pat. Nos. 5,429,694 and 5,531,850, both issued to Herrmann on Jul. 4, 1995 and Jul. 2, 1996 respectively, both of which are hereby incorporated by reference in their entirety in a manner consistent with the present invention. In such a case, the apparatus of the present invention may be adapted to maintain the unit 106 in a stretched state while conveying it to the target web 102. The applicator heads 118 may also convey the units 106 in a folded state, and may be adapted to fold the units 106 or otherwise manipulate them as they are conveyed.

A further embodiment of the invention may be adapted to cut the units 106 from a supply web 104. The applicator heads 118 may be equipped with a cutting device that severs the supply web 104 to create separate discrete units 106. Alternatively, the heads 118 may cooperate with a cutting device on the supply feeder 112 to sever units 106 from a supply web 104. For example, the heads 118 may be equipped with a raised knife edge that presses against the supply feeder 112 to sever the supply web 104, or the opposite arrangement may be employed, in which the knife edges are on the supply feeder 112 and they press against the heads 118. Ultrasonic cutters and other cutting devices may also be fitted into the applicator heads 118 or the supply feeder 112.

Other embodiments, uses and advantages of the invention will be apparent to those skilled in the art from consideration of the specification and practice of the invention disclosed herein. The specification should be considered exemplary only, and the scope of the invention is accordingly intended to be limited only by the following claims.

I claim:

1. An apparatus for assembling absorbent garments, the apparatus comprising:

an applicator adapted to rotate about an axis, the applicator having a plurality of fixed-length arms, and a plurality of heads fixed relative to one another at predetermined angles as measured relative to the axis, each head being located on a fixed-length arm, and each head being adapted to hold absorbent garment parts;

a motor adapted to rotate the applicator;

a control device adapted to control the rotational speed of the motor;

wherein the control device is operated such that each of the plurality of applicator heads travels at a first speed when any one of the heads is at a first location to pick up one or more parts moving at approximately the first speed, and each of the plurality of applicator heads travels at a second speed when any one of the heads is at a second location to deposit the one or more parts onto one or more targets moving at approximately the second speed;

wherein the angle about the axis between the first location and the second location is not substantially equal to the predetermined angles between the heads.

2. The apparatus of claim 1, wherein the plurality of heads comprises two heads.

3. The apparatus of claim 1, wherein the plurality of heads comprises vacuum gripping devices.

4. The apparatus of claim 1, wherein the plurality of heads comprises mechanical gripping devices.

5. The apparatus of claim 1, wherein the plurality of heads comprises a combination of gripping devices.

6. The apparatus of claim 1, wherein the motor is an AC servo motor.

7. The apparatus of claim 1, wherein the control device at least partially comprises an AC servo drive.

8. The apparatus of claim 1, wherein the one or more parts are absorbent core substrates and the plurality of heads are adapted to pick up, convey and deposit the absorbent core substrates.

9. The apparatus of claim 8, wherein the one or more targets are an absorbent core tissue layer or an absorbent core and the plurality of heads are adapted to deposit the absorbent core substrates onto the core tissue layer or absorbent core.

10. The apparatus of claim 1, wherein the one or more targets comprises an absorbent garment chassis layer and the plurality of heads are adapted to deposit the one or more parts onto the absorbent garment chassis layer.

11. The apparatus of claim 10, wherein the one or more parts are absorbent core subassemblies and the plurality of heads are adapted to pick up, convey and deposit the absorbent core subassemblies.

12. The apparatus of claim 10, wherein the one or more parts are grip tabs and the plurality of heads are adapted to pick up, convey and deposit the grip tabs.

13. The apparatus of claim 1, wherein the one or more targets comprises a supply of spaced apart target objects and the plurality of heads are adapted to deposit the one or more parts onto the supply of spaced apart target objects.

14. The apparatus of claim 1, wherein the one or more targets comprises a continuous web of target material and the plurality of heads are adapted to deposit the one or more parts onto the continuous web of target material.

15. The apparatus of claim 1, wherein the first speed is less than the second speed.

16. The apparatus of claim 15, wherein the first speed is equal to about 3% to about 75% of the second speed.

17. The apparatus of claim 15, wherein the first speed is equal to about 10% to about 50% of the second speed.

18. The apparatus of claim 15, wherein the first speed is equal to about 20% of the second speed.

19. The apparatus of claim 15, wherein the first speed is about 20 feet per minute to about 1,000 feet per minute and the second speed is about 50 feet per minute to about 3,000 feet per minute.

20. The apparatus of claim 15, wherein the first speed is about 40 feet per minute to about 650 feet per minute and the second speed is about 1,000 feet per minute to about 2,000 feet per minute.

21. The apparatus of claim 15, wherein the first speed is about 65 feet per minute to about 328 feet per minute and the second speed is about 1,686 feet per minute.

22. The apparatus of claim 1, wherein the first speed is greater than the second speed.

23. The apparatus of claim 1, wherein the plurality of heads further comprise cutting devices adapted to cut the one or more parts from a continuous supply web.

24. The apparatus of claim 1, wherein the one or more heads further comprise bonding devices adapted to bond the one or more parts to the one or more targets.

25. The apparatus of claim 24, wherein the bonding devices comprise portions of an ultrasonic bonding device.

26. An apparatus for assembling absorbent garments, the apparatus comprising:

a fixed-length applicator means adapted to hold absorbent garment parts, said applicator means being adapted to rotate about an axis, and having a plurality of fixed-length arms upon which are mounted a plurality of applicator heads fixed relative to one another at predetermined angles as measured relative to the axis;

a driving means for rotating the fixed-length applicator means;

a control means adapted to control the driving means;

wherein the control device is operated such that the fixed-length applicator means travels at a first speed when any one of the applicator heads is at a first location to pick up one or more parts moving at approximately the first speed, and the fixed-length applicator means travels at a second speed when any one of the applicator heads is at a second location to deposit the one or more parts onto one or more targets moving at approximately the second speed;

wherein the angle about the axis between the first location and the second location is not substantially equal to the predetermined angles between the applicator heads.

27. The apparatus of claim 26, wherein the driving means comprises an AC servo motor.

28. The apparatus of claim 26, wherein the control means at least partially comprises an AC servo drive.

* * * * *